(12) United States Patent
Emoto

(10) Patent No.: US 10,214,463 B2
(45) Date of Patent: Feb. 26, 2019

(54) PRODUCTION METHOD AND PRODUCTION APPARATUS OF α-OLEFIN OLIGOMER

(71) Applicant: MITSUBISHI CHEMICAL CORPORATION, Chiyoda-ku (JP)

(72) Inventor: Hiroki Emoto

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 15/465,118

(22) Filed: Mar. 21, 2017

(65) Prior Publication Data

US 2017/0190637 A1    Jul. 6, 2017

Related U.S. Application Data

(63) Continuation of application No. PCT/JP2015/076523, filed on Sep. 17, 2015.

(30) Foreign Application Priority Data

Sep. 22, 2014 (JP) .................................. 2014-192685

(51) Int. Cl.
*C07C 2/32* (2006.01)

(52) U.S. Cl.
CPC ............ *C07C 2/32* (2013.01); *C07C 2523/26* (2013.01); *C07C 2531/04* (2013.01); *C07C 2531/14* (2013.01); *C07C 2531/22* (2013.01)

(58) Field of Classification Search
CPC ... C07C 2/32; C07C 2531/22; C07C 2531/14; C07C 11/107
See application file for complete search history.

(56) References Cited

U.S. PATENT DOCUMENTS

| 5,744,677 | A | * | 4/1998 | Wu | ........................ B01J 31/143 |
| | | | | | 502/117 |
| 8,524,972 | B1 | | 9/2013 | Weber et al. | |

(Continued)

FOREIGN PATENT DOCUMENTS

| DE | 43 38 414 C1 | 3/1995 |
| JP | 9-77806 | 3/1997 |

(Continued)

OTHER PUBLICATIONS

International Search Report dated Dec. 1, 2015 in PCT/JP2015/076523 filed on Sep. 17, 2015 (with English translation).

(Continued)

*Primary Examiner* — In Suk C Bullock
*Assistant Examiner* — Ali Z Fadhel
(74) *Attorney, Agent, or Firm* — Oblon, McClelland, Maier & Neustadt, L.L.P.

(57) ABSTRACT

The present invention relates to a production method of an α-olefin oligomer for producing an α-olefin by performing an oligomerization reaction of an α-olefin in a reaction solvent in the presence of a catalyst in a reactor, which is a production method of an α-olefin oligomer, comprising circulating and feeding, to the reactor, a condensate liquid obtained by introducing part of gas of the gas phase part inside the reactor into a heat exchanger and cooling the gas, wherein the condensate liquid circulated and fed to the reactor is dispersed in the gas phase part inside the reactor; and a production apparatus of an α-olefin oligomer.

10 Claims, 1 Drawing Sheet

(56) References Cited

U.S. PATENT DOCUMENTS

| | | | |
|---|---|---|---|
| 9,012,577 B2 | 4/2015 | Fritz et al. | |
| 2004/0122269 A1 | 6/2004 | Van Zon et al. | |
| 2004/0122271 A1 | 6/2004 | Van Zon et al. | |
| 2005/0020866 A1* | 1/2005 | Kobayashi | C07C 2/30 585/502 |
| 2007/0185362 A1 | 8/2007 | Lattner et al. | |
| 2009/0216057 A1* | 8/2009 | Fritz | C07C 2/30 585/532 |
| 2009/0306312 A1 | 12/2009 | Fritz et al. | |
| 2012/0330078 A1 | 12/2012 | Hofmann et al. | |
| 2013/0102826 A1 | 4/2013 | Lattner et al. | |

FOREIGN PATENT DOCUMENTS

| | | | |
|---|---|---|---|
| JP | H0977806 A * | 3/1997 | C08F 2/02 |
| JP | 2003-95996 | 4/2003 | |
| JP | 2006-500411 | 1/2006 | |
| JP | 2006-500412 | 1/2006 | |
| JP | 2009-502818 | 1/2009 | |
| JP | 2009-503155 | 1/2009 | |
| JP | 2009-120588 | 6/2009 | |
| JP | 2014-177423 | 9/2014 | |
| TW | 200800848 A | 1/2008 | |
| WO | WO 2009/060342 A2 | 5/2009 | |
| WO | WO 2009/060343 A1 | 5/2009 | |
| WO | WO 2013/168099 A1 | 11/2013 | |

OTHER PUBLICATIONS

Written Opinion dated Dec. 1, 2015 in PCT/JP2015/076523 filed on Sep. 17, 2015.
Office Action dated Nov. 12, 2018 issued in corresponding patent application GC2015-30047.

\* cited by examiner

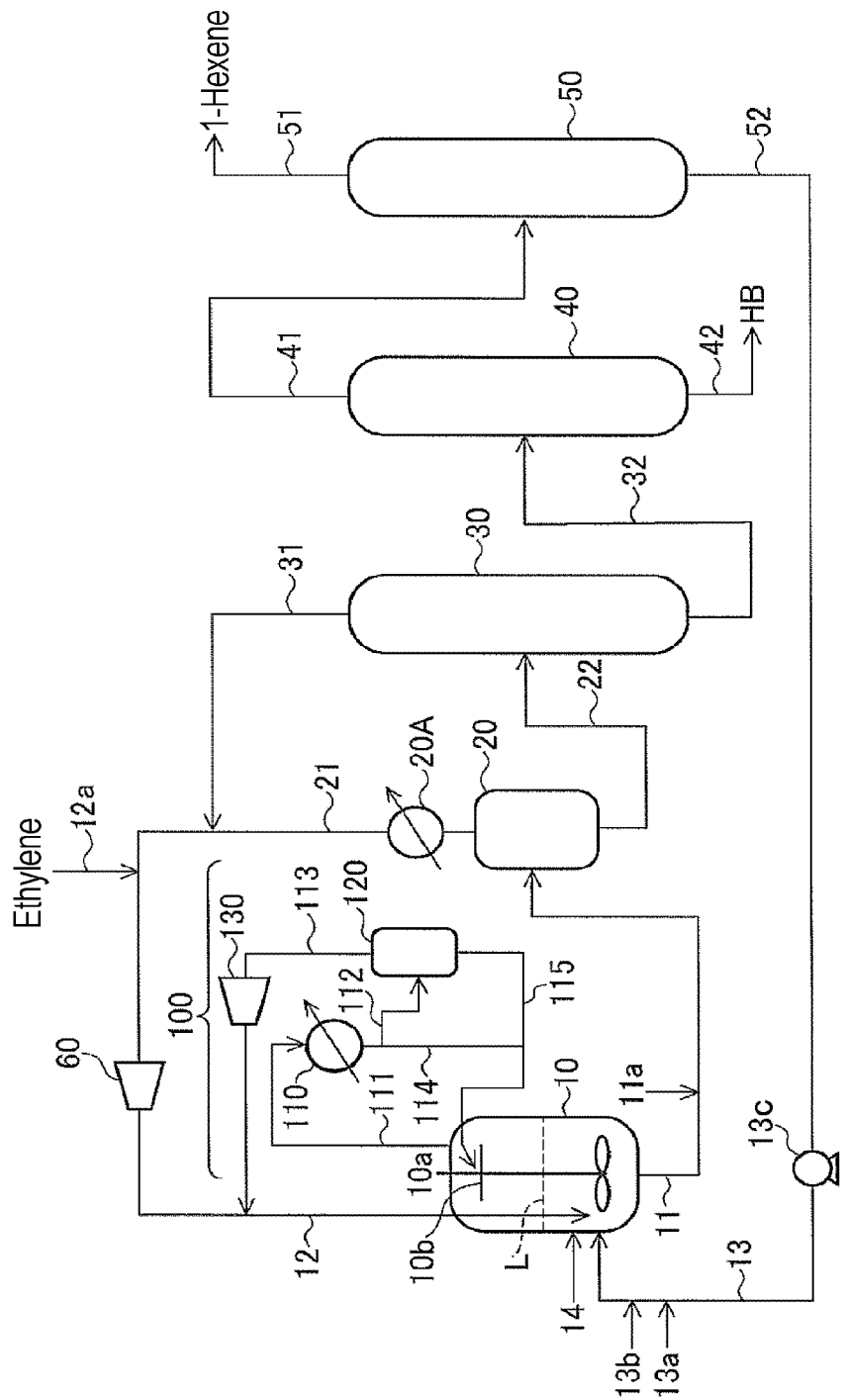

PRODUCTION METHOD AND PRODUCTION APPARATUS OF α-OLEFIN OLIGOMER

TECHNICAL FIELD

The present invention relates to a production method and a production apparatus of an α-olefin oligomer.

BACKGROUND ART

Production of an α-olefin oligomer using, as the raw material, an α-olefin such as ethylene is performed while cooling the reaction system, because the oligomerization reaction is an exothermic reaction. Therefore, various studies have been made on the industrial method for continuously producing an α-olefin oligomer while removing the heat of reaction generated in the reactor.

For example, Patent Documents 1 and 2 describe a method for producing an α-olefin oligomer having an average molecular weight of 50 to 350 by oligomerizing ethylene in the presence of a catalyst, where part of gas of the gas phase inside a reactor is cooled and condensed in a heat exchanger not in direct contact with a liquid phase by using the gas of the gas phase inside the reactor as a coolant and the heat of polymerization is removed using the condensed liquid, thereby preventing fouling of the heat exchanger.

Patent Document 3 describes a production method of an α-olefin oligomer, including introducing gas in a reactor into a heat exchanger, and circulating the gas and condensate liquid obtained from the outlet of the heat exchanger to the reactor, where the gas linear velocity of the gas phase inside the reactor is controlled to fall in a predetermined range so as to prevent a reaction solution from entrainment in the gas phase.

Patent Document 4 describes a method of cooling the top of a reactor by the use of a cooling agent such as propylene when producing an α-olefin oligomer such as 1-hexene by oligomerizing ethylene in the presence of an organic solvent and a homogenous catalyst in a reactor, where the reactor top temperature is controlled to be from about 15° C. to about 20° C. by utilizing a condenser to enhance an internal cooling cycle.

Patent Document 5 describes a technique of feeding a liquefied hydrocarbon (α-olefin) from the bottom of the reactor liquid phase at the time of oligomerization of a hydrocarbon, and Patent Document 6 describes a technique of feeding a liquefied hydrocarbon and a liquefied evaporative coolant from the bottom of the reactor liquid phase.

PATENT LITERATURE

Patent Document

[PTL 1] JP-T-2006-500411 (the term "JP-T" as used herein means a published Japanese translation of a PCT patent application)
[PTL 2] JP-T-2006-500412
[PTL 3] JP-A-2009-120588 (the term "JP-A" as used herein means an "unexamined published Japanese patent application")
[PTL 4] JP-T-2009-503155
[PTL 5] International Publication No. 09/060342
[PTL 6] International Publication No. 09/060343

SUMMARY OF INVENTION

Problems that the Invention is to Solve

As the method for cooling the reaction system in a oligomerization reaction of an α-olefin to obtain an α-olefin oligomer by using, as the raw material, an α-olefin such as ethylene, a method where gas of the gas phase inside a reactor, containing a very slight amount of a foulant such as byproduct polymer or deactivated catalyst, is withdrawn from the reactor and cooled/condensed by a heat exchanger (condenser) and the condensate liquid and uncondensed gas are circulated to the reactor, is preferred from the standpoint of preventing fouling of the heat exchanger. In addition, at this time, the uncondensed gas is preferably fed to the bottom of the liquid phase part of the reactor.

However, in this method, bursting of a bubble of gas vaporized by the heat of polymerization or bubbles of the vaporized gas and an uncondensed gas occurs at the gas-liquid interface in the reactor, as a result, a reaction solution mist is generated in the gas phase part inside the reactor. The mist is withdrawn from the reactor by entrainment together with gas, reaches the heat exchanger, and fouls the cooling heat transfer surface of the heat exchanger, particularly, the inlet part thereof, disturbing a long-term stable operation.

When the heat exchanger is fouled, the heat-exchange efficiency is inhibited or the ventilation resistance increases and in an extreme case, the operation cannot be continued. Therefore, the heat exchanger needs to be cleaned by stopping the operation periodically or as required, making continuous operation impossible.

The present invention has been made to solve the above-described problems in the production process of an α-olefin oligomer.

An object of the present invention is to provide a production method and a production apparatus of an α-olefin oligomer, where at the time of producing an α-olefin oligomer by an oligomerization reaction of an α-olefin, gas of the gas phase inside a reactor is withdrawn and cooled by a heat exchanger and the obtained condensate liquid and an uncondensed gas are circulated and fed to the reactor and deprived of heat, which are a production method and a production apparatus of an α-olefin oligomer, ensuring that the reaction solution mist generated in the gas phase part of the reactor can be prevented from reaching the heat exchanger by entrainment together with gas and fouling the heat exchanger and in turn, a long-term stable operation can be achieved.

Means for Solving the Problems

As a result of intensive studies to attain the object above, the present inventors have found that when a liquid substantially free of a foulant is dispersed as droplets in the gas phase part of a reactor, the reaction solution mist can be captured by the droplet and discharge of the mist from the reactor together with gas of the gas phase part can be inhibited, as a result, fouling of a heat exchange can be prevented and a long-term stable operation can be achieved. In addition, it has been found that the liquid substantially free of a foulant is preferably a condensate liquid obtained in the heat exchanger and/or a reaction solvent separated and recovered from the reaction product liquid.

That is, the gist of the present invention resides in the following [1] to [14].

[1] A production method of an α-olefin oligomer for producing an α-olefin oligomer by performing an oligomerization reaction of an α-olefin in a reaction solvent in the presence of a catalyst in a reactor, which is a production method of an α-olefin oligomer, comprising circulating and feeding, to said reactor, a condensate liquid obtained by introducing part of gas of the gas phase part inside said reactor into a heat exchanger and cooling the gas, wherein said condensate liquid circulated and fed to said reactor is dispersed in the gas phase part inside said reactor.

[2] The production method of an α-olefin oligomer as described in the above [1], wherein said heat exchanger is arranged outside of said reactor.

[3] The production method of an α-olefin oligomer as described in the above [1] or [2], wherein said condensate liquid is dispersed as droplets.

[4] The production method of an α-olefin oligomer as described in any one of the above [1] to [3], wherein said condensate liquid is dispersed as droplets by means of an atomizer.

[5] The production method of an α-olefin oligomer as described in claim 4], wherein the system of said atomizer is one or more systems selected from the group consisting of a centrifugal force system, a shear force system and a pressure system.

[6] The production method of an α-olefin oligomer as described in any one of the above [1] to [5], wherein the gas outlet temperature of the gas phase part of said reactor is lower by 8° C. or more than the liquid phase temperature of said reactor.

[7] The production method of an α-olefin oligomer as described in any one of the above [1] to [5], wherein the inlet temperature of said heat exchanger is lower by 8° C. or more than the liquid phase temperature of said reactor.

[8] The production method of an α-olefin oligomer as described in any one of the above [1] to [7], wherein an uncondensed gas obtained from said heat exchanger is circulated and fed to the liquid phase part of said reactor.

[9] The production method of an α-olefin oligomer as described in any one of the above [1] to [8], wherein said catalyst is composed of a combination of a chromium-containing compound, a nitrogen-containing compound (b), and an aluminum-containing compound (c).

[10] The production method of an α-olefin oligomer as described in [9], wherein said catalyst further contains a halogen-containing compound (d).

[11] The production method of an α-olefin oligomer as described in any one of the above [1] to [10], wherein said α-olefin is ethylene.

[12] A production apparatus of an α-olefin oligomer for producing an α-olefin oligomer by performing an oligomerization reaction of an α-olefin, comprising a reactor fed with a catalyst, an α-olefin and a reaction solvent for performing an oligomerization reaction of the α-olefin, a heat exchanger for cooling gas withdrawn from the gas phase part inside said reactor to obtain a condensate liquid, a circulatory feed unit for circulating and feeding, to said reactor, the condensate liquid obtained in said heat exchanger, and a droplet dispersion unit for dispersing, in the gas phase part inside said reactor, at least either one of a condensate liquid from said circulatory feed unit and a reaction solvent from said circulatory feed unit.

[13] The production apparatus of an α-olefin oligomer as described in the above [12], wherein said droplet dispersion unit is an atomizer provided in the gas phase part inside said reactor.

[14] A method for producing an α-olefin oligomer, comprising performing an oligomerization reaction of an α-olefin in a reaction solvent in the presence of a catalyst in a reactor to produce an α-olefin oligomer, wherein at the time of introducing at least part of gas of the gas phase part inside said reactor into a heat exchanger outside of said reactor and cooling the gas, the outlet temperature of the gas phase part inside said reactor is lower by 8° C. or more than the temperature of the liquid phase of said reactor.

Advantageous Effects of Invention

According to the present invention, in the production process of an α-olefin oligomer, fouling of a heat exchanger for cooling the gas of the gas phase part of a reactor can be prevented and a long-term stable operation can be achieved.

BRIEF DESCRIPTION OF THE DRAWING

FIG. 1 is a process flow diagram showing one embodiment of the production method and the production apparatus of an α-olefin oligomer of the present invention.

DESCRIPTION OF EMBODIMENTS

The mode for carrying out the present invention is described in detail below. The present invention is not limited to the following embodiment and can be implemented by making various modifications therein within the scope of the gist. In addition, the drawing used is for describing this embodiment and does not show the actual size.

[Production Step of α-Olefin Oligomer]

The production step of an α-olefin oligomer according to the present invention is described by referring to FIG. 1 showing one example of the production method and the production apparatus of an α-olefin oligomer of the present invention. The raw material α-olefin, the catalyst, the reaction solvent, etc. for use in the present invention are described later.

In the following, the production of 1-hexene (a trimer of ethylene) using ethylene as the raw material α-olefin is mainly described for example, but the present invention is not limited to the production of 1-hexene from ethylene.

In the apparatus of FIG. 1, a reactor 10 of a complete mixing and stirring type for oligomerizing ethylene in the presence of a catalyst such as chromium-based catalyst, and a reflux condensation system 100 for cooling and condensing a vapor component vaporized from an ethylene gas and a liquid phase in the reactor 10 are provided as main devices.

In addition, the apparatus is provided with a degassing tank 20 for separating an unreacted ethylene gas from the reaction product liquid withdrawn from the reactor 10, an ethylene separation column 30 for distilling out ethylene in the reaction product liquid withdrawn from the degassing tank 20, a high boiling separation column 40 for separating a high boiling-point substance (hereinafter, sometimes referred to as "HB" (high boiler)) in the reaction product liquid withdrawn from the ethylene separation column 30, and a hexene separation column 50 for distilling the distillate liquid withdrawn from the top of the high boiling separation column 40 to distill out 1-hexene.

In the apparatus shown in FIG. 1, the raw material ethylene is continuously fed to the reactor 10 from an ethylene feed pipe 12a through a compressor 60 and a first feed pipe 12. Into the compressor 60, unreacted ethylene separated in the degassing tank 20 and a condenser 20A is introduced through circulation piping 21 and at the same time, ethylene separated in the ethylene separation column 30 is introduced through circulation piping 31, which are circulated as the raw material ethylene to the reactor 10 together with ethylene from the ethylene feed pipe 12a.

On the other hand, a reaction solvent used for the oligomerization reaction of ethylene is fed to the reactor 10 from a second feed pipe 13. This reaction solvent is a solvent separated and recovered in the later-stage hexene separation column 50. To the second feed pipe 13, out of the catalyst components, a transition metal-containing compound (a) and a nitrogen-containing compound (b) are fed through a catalyst feed pipe 13a, and a halogen-containing compound (d) is fed through a catalyst feed pipe 13b, which are introduced into the reactor 10 together with the reaction solvent.

In addition, an aluminum-containing compound (c) is introduced directly into the reactor 10 from a third feed pipe 14. The aluminum-containing compound (c) may also be diluted with the reaction solvent in the second feed pipe 13 before the feeding of catalyst components from the catalyst feed pipes 13a and 13b and then fed to the reactor 10 (not shown). These catalyst components are preferably fed to the liquid phase part in the reactor 10.

Incidentally, at the time of circulating and feeding the reaction solvent from the hexane separation column 50 to the reactor 10, at least part of the reaction solvent in the second feed pipe 13 before the feeding of catalyst components from the catalyst feed pipes 13a and 13b may be fed by dispersion as droplets to the gas phase part of the reactor 10. With respect to the feed mode, the same mode as that of a condensate liquid from the later-described heat exchanger 110 may be employed.

The reactor 10 includes, for example, a reactor of a conventionally known type equipped with a stirrer 10a, a baffle, a jacket, etc. As the stirrer 10a, a stirring blade of, for example, a paddle, Pfaudler, propeller or turbine type is used in combination with a baffle such as flat plate, cylinder or hairpin coil.

In FIG. 1, the reactor 10 is provided with an atomizer 10b for dispersing the condensate liquid from a reflux condensation system 100 as droplets in the gas phase part inside the reactor 10.

The dispersion means that the liquid fed to the gas phase part of the reactor through piping, etc. is in the state of being divided into a plurality of droplets and scattered or is sprayed.

In FIG. 1, the dashed line L indicates the gas-liquid interface.

The reflux condensation system 100 is provided with a heat exchanger 110 where an ethylene gas introduced into the liquid phase of the reactor 10 and an evaporated vapor from the liquid phase are introduced through piping 111 and cooled/condensed, a gas-liquid separator 120 where part of the condensate liquid and uncondensed gas component obtained in the heat exchanger 110 are introduced through piping 112 and separated into a condensate liquid and a gas component, and a blower 130 for introducing the gas component separated in the gas-liquid separator 120 into the liquid phase of the reactor 10 through piping 113 and the first feed pipe 12.

The condensate liquid obtained in the heat exchanger 110 and the condensate liquid separated in the gas-liquid separator 120 are circulated and fed to the atomizer 10b (in FIG. 1, an atomizer of a rotating disc spray system) provided in the gas phase part inside the reactor 10 through piping 114 and piping 115, respectively, and dispersed as droplets.

As for the operation conditions of the reactor 10, the reaction temperature (measured liquid phase temperature) is usually from 50 to 250° C., preferably from 100 to 200° C., more preferably from 120 to 170° C. The reaction pressure is usually from normal pressure to 250 kg/cm$^2$ (24.5 MPa), preferably from 5 to 150 kg/cm$^2$ (from 0.49 to 14.7 MPa), more preferably from 10 to 100 kg/cm$^2$ (from 0.98 to 9.8 MPa).

The trimerization reaction of ethylene is preferably performed such that the molar ratio of 1-hexene to ethylene in the reaction solution inside the reactor 10 [(1-hexene in reaction solution)/(ethylene in reaction solution)] becomes from 0.05 to 1.5, more preferably from 0.10 to 1.0.

Accordingly, in the case of continuous reaction, the catalyst concentration, reaction pressure or other conditions are adjusted so that the molar ratio of ethylene and 1-hexene in the reaction solution can fall in the range above, and in the case of batch reaction, the reaction is preferably stopped at the time when the molar ratio is in the range above. Such an operation tends to suppress the by-production of components having a boiling point higher than that of 1-hexene and further increase the selectivity for 1-hexene.

The gas linear velocity of the gas phase part inside the reactor 10 is preferably from 0.1 to 10.0 cm/s, more preferably from 0.3 to 5.0 cm/s, still more preferably from 0.5 to 3.0 cm/s.

By controlling the gas linear velocity of the gas phase part of the reactor 10 to fall in the range above, at the time of delivering the ethylene gas in the reactor 10 and the vapor component vaporized from the liquid phase to the heat exchanger 110, the entrainment of the reaction solution tends to be suppressed.

The gas outlet temperature of the gas phase part of the reactor is preferably lower by 8° C. or more, more preferably by 10° C. or more, still more preferably by 10 to 40° C., yet still more preferably by 15 to 35° C., than the liquid phase temperature of the reactor 10.

When the gas outlet temperature of the gas phase part of the reactor is lower by 8° C. or more than the liquid phase temperature of the reactor, a condensate liquid is generated from gas of the gas phase part by using the reaction solution mist as a nucleus and therefore, the mist diameter becomes large, making it easy to achieve gas-liquid separation in the gas phase part of the reactor, as a result, the number of reaction solution mists in the outlet gas of the gas phase part of the reactor tends to be decreased.

However, it is not necessary to excessively lower the gas outlet temperature of the gas phase part of the reactor. The reason therefor is because the area of the cooling heat transfer surface of the heat exchanger 110 needs to be increased and/or the coolant needs to be changed from water to a liquefied evaporative coolant, etc., leading to a rise in the construction cost.

Here, the gas outlet temperature of the gas phase part of the reactor, when it is equal to the inlet temperature of the heat exchanger, may be measured by the inlet temperature of the heat exchanger. Because, the temperature of vapor fed to the heat exchanger is preferably lower by 8° C. or more, more preferably by 10° C. or more, still more preferably by 10 to 40° C., yet still more preferably by 15 to 35° C., than the liquid phase temperature of the reactor 10.

The diameter of the droplet dispersed by the atomizer 10b inside the reactor 10 and the method for feeding by dispersion as droplets are not particularly limited, but the following embodiments are preferred.

In the case where a condensate generated on a member present in the gas phase part of the reactor naturally falls as a stick without the aid of any dispersion means, the effects of the present invention are not exerted. Because, neither the reaction solution mist can be captured nor the gas outlet temperature of the gas phase part of the reactor can be lowered.

The droplet diameter is usually from 0.05 to 5 mm, preferably from 0.1 to 3 mm, more preferably from 0.3 to 2 mm, still more preferably from 0.5 to 1.5 mm. If the droplet diameter is too small, the droplet does not fall to the liquid phase part of the reactor 10 and is entrained together with gas of the gas phase part of the reactor 10 and therefore, there is a tendency that the heat exchanger 110 is fouled and at the same time, the liquid load on the heat exchanger 110 becomes excessively high, making the operation difficult. If the droplet diameter is too large, the number of droplets is relatively decreased and since the total surface area of all droplets becomes small, the effect of capturing the reaction solution mist tends to be reduced.

The method for dispersing droplets is not particularly limited, but as shown in FIG. 1, an atomizer 10b is preferably used. The system of the atomizer is not particularly limited, but a centrifugal force system, a shear force system, a pressure system, etc. are preferred. Among these, in view of the droplet dispersion efficiency, a centrifugal force system is more preferred.

The centrifugal force system is more preferably a rotating disc spray system. In addition, the pressure system is preferably a nozzle spray system.

In the atomizer 10b of a rotating disc spray system, a liquid is supplied to the central part of a rotating disc, and atomization of the liquid is performed in the outer peripheral part of the disc by the centrifugal force. In the case of an atomizer 10b of a rotating disc spray system, the ratio of the diameter of the rotating disk of the atomizer 10b to the diameter of the reactor 10 is usually from 0.1 to 0.8, preferably from 0.2 to 0.6, more preferably from 0.3 to 0.5.

On the rotating disc, a plurality of weirs may be provided along the radial direction, and by employing this configuration, droplet formation can be efficiently achieved.

The nozzle spray system includes three systems of 1) pressurized nozzle, 2) two-fluid nozzle, and 3) pressurized two-fluid nozzle.

In the pressurized nozzle spray system, a pressurized liquid is introduced into a spin chamber called a core, and the liquid subject to a turning force passes through orifices, forming a film, and is thereby atomized.

In the two-fluid nozzle spray system, the liquid is put into contact with a compressed gas and sheared, thereby performing atomization.

The pressurized two-fluid nozzle spray system is a system making use of characteristic features of the above-described two kinds of nozzles, and by providing a pressurized nozzle in the central part and flowing a low-pressure assist gas from the periphery thereof, the atomization can be accelerated.

Such an atomizer 10b is provided, in the gas phase part inside the reactor 10, usually approximately from 0.3 to 3 m, preferably approximately from 0.5 to 2 m, above the gas-liquid interface L.

The amount of liquid supplied to the atomizer is, in terms of the volume ratio, preferably from 1 to 50%, more preferably from 2 to 30%, still more preferably from 4 to 20%, relative to the amount of gas rising from the gas-liquid interface part of the reactor. If the amount of liquid supplied is too small, the reaction solution mist tends to be hardly captured, and if the amount of liquid is too large, the droplet diameter is more increased due to coalescence of droplets with each other, and this is not efficient.

As the heat exchanger 110, a vertical or horizontal multitubular heat exchanger used for the cooling of a fluid to be condensed is employed. Such a heat exchanger is known as a general reflux condenser, and in this embodiment, a vertical multitubular heat exchanger is preferred.

The material constituting the heat exchanger 110 is not particularly limited and includes, for example, carbon steel, copper, titanium alloy, SUS304, SUS316 and SUS316L which are known as a material constituting a normal reflux condenser. The material is appropriately selected according to the process. Incidentally, the heat transfer area of the heat exchanger 110 is appropriately determined according to, for example, the degree of heat removal load or the system for load control.

The action of the reflux condenser system 100 is as follows.

A mixed gas of an ethylene gas introduced into the liquid phase part inside the reactor 10 and an evaporated vapor resulting from vaporization of part of the liquid phase due to the polymerization heat produced by an oligomerization reaction of ethylene in the reactor 10 is fed to the heat exchanger 110 by piping 111.

It is preferred that the piping 111 is thermally insulated and kept warm so as to prevent the pipe from clogging by polyethylene produced starting from the reaction solution mist attached to the inner surface of piping or is a cooling piping layout, e.g., double pipe, so as to aggressively generate a condensate liquid on the inner surface of piping and prevent attachment of the reaction solution mist.

The mixed gas fed to the heat exchanger 110 is cooled/condensed by cooling water (not shown) to usually from 30 to 100° C., preferably from 45 to 95° C., more preferably from 55 to 90° C., and the condensate liquid is again circulated and fed to the reactor 10 by piping 114.

In addition, part of the uncondensed gas and condensate liquid obtained from the heat exchanger 110 is delivered to the gas-liquid separator 120 by piping 112 and separated into ethylene and a condensate liquid in the gas-liquid separator 120, and ethylene is circulated and fed to the liquid phase part of the reactor 10 by the blower 130 through piping 113 and the first feed pipe 12. The condensate liquid is circulated and fed to the reactor 10 through piping 115.

Here, the condensate liquid obtained from the heat exchanger 110 and the condensate liquid separated in the gas-liquid separator 120 are introduced into the atomizer 10b (in FIG. 1, a rotating disc spray system is shown) placed in the gas phase of the reactor 10 through piping 114 and piping 115, respectively, and atomized. The atomized condensate liquid is dispersed as droplets in the gas phase part of the reactor 10 and falls onto the liquid level while countercurrently contacting with a rising gas. In this way, the condensate liquid is circulated and fed to the gas phase part of the reactor 10 and dispersed as droplets, whereby a foulant such as byproduct polymer can be prevented from attaching to the heat exchanger 110.

The reasons therefor are estimated to be the following (1) and (2).

(1) A mist containing a catalyst component or ethylene is present in the gas generated by vaporization of the reaction solution in the reactor 10. The mist is put into contact with a condensate liquid droplet in the gas phase part inside the reactor 10 and thereby absorbed in the condensate liquid droplet and thereafter, falls onto the liquid level of the reaction solution together with the condensate liquid droplet.

(2) A miniaturized, low-temperature condensate liquid droplet contacts with a high-temperature rising gas in the gas phase part inside the reactor 10, as a result, the high-temperature gas is cooled and a condensate liquid is generated from the gas. Since the condensation here occurs by using the reaction solution mist as a nucleus, the mist diameter is increased, and the mist increased in the diameter falls onto the liquid level of the reaction solution without being entrained by the gas.

For the reasons (1) and (2), the reaction solution mist generated in the gas phase part of the reactor is prevented from reaching the heat exchanger by entrainment together with the gas and fouling the heat exchanger.

Incidentally, the reaction solvent separated from the reaction product liquid in the later-stage hexane separation column 50 is caused to contain substantially no foulant by the separation and distillation in the preceding stage and therefore, when droplets of the reaction solvent separated and recovered in the hexane separation column 50 are dispersed in the gas phase part of the reactor 10, a byproduct polymer, etc. can be likewise inhibited from attaching to the heat exchanger 110.

In this way, in the present invention, fouling of the heat exchanger 110 can be prevented and therefore, the operation can be stably continued over a long period of time, but when a foulant such as byproduct polymer is attached to the heat exchanger 110 and fouling proceeds, the heat exchanger 110 is cleaned by stopping the operation.

In this case, the reaction solvent separated from the reaction product liquid obtained from the outlet of the reactor 10 is usually used for the cleaning liquid. The temperature of the cleaning liquid is usually 110° C. or more, preferably from 115 to 170° C. The pressure at the time of cleaning is preferably lower and is usually 71 kg/cm$^2$ (7.0 MPa) or less, preferably 31 kg/cm$^2$ (3.0 MPa) or less, more preferably 10 kg/cm$^2$ (0.98 MPa) or less. The cleaning liquid is supplied to the inside of the heat exchanger 110 by means of a spray nozzle and cleans the inside of the heat exchanger 110 fouled due to the effect of entrainment of the reaction solution.

According to the present invention, the frequency of cleaning of the heat exchanger 110 can be greatly reduced.

The reaction product liquid reaching the predetermined conversion ratio in the reactor 10 is continuously withdrawn from the bottom of the reactor 10 through piping 11 and fed to the degassing tank 20. At this time, the trimerization reaction of ethylene is stopped by a catalyst deactivator such as 2-ethylhexanol supplied from a deactivator feed pipe 11a. The unreacted ethylene degassed in the degassing tank 20 is circulated and fed to the reactor 10 from the top of the degassing tank 20 through the heat exchanger 20A, the circulation piping 21, the compressor 60 and the first feed pipe 12. In addition, the reaction product liquid after degassing of unreacted ethylene is withdrawn from the bottom of the degassing tank 20.

The operation conditions of the degassing tank 20 are a temperature of usually from 30 to 240° C., preferably from 80 to 190° C., and a pressure of usually from normal pressure to 150 kg/cm$^2$ (14.7 MPa), preferably from normal pressure to 90 kg/cm$^2$ (8.8 MPa).

The reaction product liquid withdrawn from the bottom of the degassing tank 20 is fed to the ethylene separation column 30 through piping 22. In the ethylene separation column 30, ethylene is distilled out and separated from the top by distillation, and this ethylene is circulated and fed to the reactor 10 through the circulation piping 31 and the first feed pipe 12. In addition, the reaction product liquid after removal of ethylene is withdrawn from the bottom of the column.

The operation conditions of the ethylene separation column 30 are a top pressure of usually from normal pressure to 30 kg/cm$^2$ (from 0.1 to 2.9 MPa), preferably from normal pressure to 20 kg/cm$^2$ (from 0.1 to 2.0 MPa), and a reflux ratio (R/D) of usually from 0 to 500, preferably from 0.1 to 100.

The reaction product liquid after distillation out and separation of ethylene in the ethylene separation column 30 is withdrawn from the bottom of the ethylene separation column 30 and fed to the high boiling separation column 40 by piping 32. In the high boiling separation column 40, high boiling-point components (HB: high boiler) are withdrawn from the bottom through piping 42. In addition, a distillate after separation of high boiling components is withdrawn from the top through piping 41.

The operation conditions of the high boiling separation column 40 are a top pressure of usually from 0.1 to 10 kg/cm$^2$ (from 0.01 to 0.98 MPa), preferably from 0.5 to 5 kg/cm$^2$ (from 0.05 to 0.49 MPa), and a reflux ratio (R/D) of usually from 0 to 100, preferably from 0.1 to 20.

Subsequently, the distillation liquid withdrawn from the top of the high boiling separation column 40 is fed to the hexene separation column 50 by piping 41. In the hexene separation column 50, 1-hexene is distilled out from the top through piping 51 by distillation.

In addition, the reaction solvent, for example, n-heptane, is withdrawn from the bottom of the hexene separation column 50, and circulated and fed as a reaction solvent to the reactor 10 through solvent circulation piping 52, a pump 13c and the second feed pipe 13. As with the condensate liquid, the reaction solvent circulated and fed to the reactor 10 may be dispersed as droplets in the gas phase part inside the reactor.

The operation conditions of the hexene separation column 50 are a top pressure of usually from 0.1 to 10 kg/cm$^2$ (from 0.01 to 0.98 MPa), preferably from 0.5 to 5 kg/cm$^2$ (from 0.05 to 0.49 MPa), and a reflux ratio (R/D) of usually from 0 to 100, preferably from 0.2 to 20.

[α-Olefin]

In the production method of an α-olefin oligomer of the present invention, the α-olefin used as a raw material includes, for example, a substituted or unsubstituted α-olefin having a carbon number of 2 to 8. Specific examples of such an α-olefin include ethylene, propylene, 1-butene, 1-hexene, 1-octene, 3-methyl-1-butene and 4-methyl-1-pentene. Among others, the raw material α-olefin for use in the present invention is preferably ethylene.

The α-olefin oligomer as the product is an α-olefin obtained by oligomerization reaction (dimerization to pentamerization) of the above-described raw material α-olefin and when ethylene is used as the raw material, 1-butene, 1-hexene, 1-octene and 1-decene, which are oligomers (dimer to pentamer) of ethylene, can be obtained. Among others, 1-hexene as a trimer of ethylene and/or 1-octene as a tetramer of ethylene can be obtained with high yield and high selectivity.

In addition, in the case of using ethylene as the raw material, the raw material may contain impurity components other than ethylene. Specific impurity components include, for example, methane, ethane, nitrogen, oxygen, water, acetylene, carbon dioxide, carbon monoxide, and hydrogen sulfide.

As for methane, ethane and nitrogen, the content is preferably 0.1 mol % or less relative to the raw material ethylene. As for oxygen, water, acetylene, carbon dioxide, carbon monoxide and a sulfur content such as hydrogen sulfide, the content is preferably 1 mol ppm or less relative to the raw material ethylene.

[Catalyst]

The catalyst for use in the present invention is not particularly limited as long as it is a catalyst capable of bringing about an oligomerization reaction of the raw material α-olefin and producing an α-olefin oligomer, but a catalyst containing (c) an aluminum-containing compound is preferred.

A catalyst using a transition metal-containing compound (a), a nitrogen-containing compound (b) and an aluminum-containing compound (c) as constituent components of the catalyst and being a chromium-based catalyst composed of components derived from these compounds, is more preferred. In addition, from the standpoint of enhancing the catalytic activity and the selectivity for the target α-olefin oligomer, it is still more preferable to contain (d) a halogen-containing compound as a constituent component of the catalyst.

[Transition Metal-Containing Compound (a)]

The metal contained in the transition metal-containing compound (a) (hereinafter, sometimes referred to as "catalyst component (a)") that is preferably used as a constituent component of the catalyst of the present invention, is not particularly limited as long as it is a transition metal, but among others, a transition metal of Groups 4 to 6 of the periodic table is preferably used.

Specifically, one or more kinds of metals selected from the group consisting of chromium, titanium, zirconium, vanadium and hafnium are preferred, chromium or titanium is more preferred, and chromium is most preferred.

The transition metal-containing compound (a) is one or more compounds usually represented by the formula MeZn. In the formula MeZn, Me is a transition metal element, Z is an arbitrary organic or inorganic group or an electronegative atom, and n is an integer of 1 to 6, preferably 2 or more. When n is 2 or more, each Z may be the same as or different from every other Z.

The organic group includes a hydrocarbon group having a carbon number 1 to 30, which may have a substituent, and specifically includes, for example, a carbonyl group, an alkoxy group, a carboxyl group, a β-diketonate group, a β-ketocarboxyl group, β-ketoester group, and an amide group.

The inorganic group includes, for example, a metal salt-forming group such as nitric acid group and sulfuric acid group. The electronegative atom includes, for example, oxygen and a halogen. Incidentally, a transition metal-containing compound (a) in which a halogen atom is contained, is not encompassed by the later-described halogen-containing compound (d).

Specific examples of the transition metal-containing compound in which the transition metal is chromium (hereinafter, sometimes referred to as "chromium-containing compound") include chromium(IV)-tert-butoxide, chromium (III) acetylacetonate, chromium(III) trifluoroacetylacetonate, chromium(III) hexafluoroacetylacetonate, chromium(III) (2,2,6,6-tetramethyl-3,5-heptanedionate), $Cr(PhCOCHCOPh)_3$ (wherein Ph represents a phenyl group), chromium(II) acetate, chromium(III) acetate, chromium(III) 2-ethylhexanoate, chromium(III) benzoate, chromium(III) naphthenate, chromium(III) heptanoate, $Cr(CH_3COCHCOOCH_3)_3$, chromous chloride, chromic chloride, chromous bromide, chromic bromide, chromous iodide, chromic iodide, chromous fluoride, and chromic fluoride.

Specific examples of the transition metal-containing compound in which the transition metal is titanium (hereinafter, sometimes referred to as "titanium-containing compound") include $TiCl_4$, $TiBr_4$, $TiI_4$, $TiBrCl_3$, $TiBr_2Cl_2$, $Ti(OC_2H_5)_4$, $Ti(OC_2H_5)_2Cl_2$, $Ti(O-n-C_3H_7)_4$, $Ti(O-n-C_3H_7)_2Cl_2$, $Ti(O-iso-C_3H_7)_4$, $Ti(O-iso-C_3H_7)_2Cl_2$, $Ti(O-n-C_4H_9)_4$, $Ti(O-n-C_4H_9)_2Cl_2$, $Ti(O-iso-C_4H_9)_4$, $Ti(O-iso-C_4H_9)_2Cl_2$, $Ti(O-tert-C_4H_9)_4$, $Ti(O-tert-C_4H_9)_2Cl_2$, $TiCl_4(thf)_2$ (in this chemical formula, thf represents tetrahydrofuran), $Ti[(CH_3)_2N]_4$, $Ti[(C_2H_5)_2N]_4$, $Ti[(n-C_3H_7)_2N]_4$, $Ti[(iso-C_3H_7)_2N]_4$, $Ti[(n-C_4H_9)_2N]_4$, $Ti[(tert-C_4H_9)_2N]_4$, $Ti(OSO_3CH_3)_4$, $Ti(OSO_3C_2H_5)_4$, $Ti(OSO_3C_3H_7)_4$, $Ti(OSO_3C_4H_9)_4$, $TiCp_2Cl_2$, $TiCp_2ClBr$ (in this chemical formula, Cp represents a cyclopentadienyl group; the same applies to the zirconium-containing compound below), $Ti(OCOC_2H_5)_4$, $Ti(OCOC_2H_5)_2Cl_2$, $Ti(OCOC_3H_7)_4$, $Ti(OCOC_3H_7)_2Cl_2$, $Ti(OCOC_3H_7)_4$, $Ti(OCOC_3H_7)_2Cl_2$, $Ti(OCOC_4H_9)_4$ and $Ti(OCOC_4H_9)_2Cl_2$.

Specific examples of the transition metal-containing compound in which the transition metal is zirconium (hereinafter, sometimes referred to as "zirconium-containing compound") include $ZrCl_4$, $ZrBr_4$, $ZrI_4$, $ZrBrCl_3$, $ZrBr_2Cl_2$, $Zr(OC_2H_5)_4$, $Zr(OC_2H_5)_2Cl_2$, $Zr(O-n-C_3H_7)_4$, $Zr(O-n-C_3H_7)_2Cl_2$, $Zr(O-iso-C_3H_7)_4$, $Zr(O-iso-C_3H_7)_2Cl_2$, $Zr(O-n-C_4H_9)_4$, $Zr(O-n-C_4H_9)_2Cl_2$, $Zr(O-iso-C_4H_9)_4$, $Zr(O-iso-C_4H_9)_2Cl_2$, $Zr(O-tert-C_4H_9)_4$, $Zr(O-tert-C_4H_9)_2Cl_2$, $Zr[(CH_3)_2N]_4$, $Zr[(C_2H_5)_2N]_4$, $Zr[(n-C_3H_7)_2N]_4$, $Zr[(iso-C_3H_7)_2N]_4$, $Zr[(n-C_4H_9)_2N]_4$, $Zr[(tert-C_4H_9)_2N]_4$, $Zr(OSO_3CH_3)_4$, $Zr(OSO_3C_2H_5)_4$, $Zr(OSO_3C_3H_7)_4$, $Zr(OSO_3C_4H_9)_4$, $ZrCp_2Cl_2$, $ZrCp_2ClBr$, $Zr(OCOC_2H_5)_4$, $Zr(OCOC_2H_5)_2Cl_2$, $Zr(OCOC_3H_7)_4$, $Zr(OCOC_3H_7)_2Cl_2$, $Zr(OCOC_3H_7)_4$, $Zr(OCOC_3H_7)_2Cl_2$, $Zr(OCOC_4H_9)_4$, $Zr(OCOC_4H_9)_2Cl_2$, $ZrCl_2(HCOCFCOF)_2$ and $ZrCl_2(CH_3COCFCOCH_3)_2$.

Specific examples of the transition metal-containing compound in which the transition metal is hafnium (hereinafter, sometimes referred to as "hafnium-containing compound") include dimethylsilylene bis{1-(2-methyl-4-isopropyl-4H-azulenyl)}hafnium dichloride, dimethylsilylene bis{1-(2-methyl-4-phenyl-4H-azulenyl)}hafnium dichloride, dimethylsilylene bis[1-{2-methyl-4-(4-chlorophenyl)-4H-azulenyl}]hafnium dichloride, dimethylsilylene bis[1-{2-methyl-4-(4-fluorophenyl)-4H-azulenyl}]hafnium dichloride, dimethylsilylene bis[1-{2-methyl-4-(3-chlorophenyl)-4H-azulenyl}]hafnium dichloride, dimethylsilylene bis[1-{2-methyl-4-(2,6-dimethylphenyl)-4H-azulenyl}]hafnium dichloride, dimethylsilylene bis{1-(2-methyl-4,6-diisopropyl-4H-azulenyl)}hafnium dichloride, diphenylsilylene bis{1-(2-methyl-4-phenyl-4H-azulenyl)}hafnium dichloride, methylphenylsilylene bis{1-(2-methyl-4-phenyl-4H-azulenyl)}hafnium dichloride, methylphenylsilylene bis[1-{2-methyl-4-(1-naphthyl)-4H-azulenyl}]hafnium dichloride, dimethylsilylene bis{1-(2-ethyl-4-phenyl-4H-azulenyl)}hafnium dichloride, dimethylsilylene bis[1-{2-ethyl-4-(1-anthracenyl)-4H-azulenyl}]hafnium dichloride, dimethylsilylene bis[1-{2-ethyl-4-(2-anthracenyl)-4H-azulenyl}]hafnium dichloride, dimethylsilylene bis[1-{2-ethyl-4-(9-phenanthryl)-4H-azulenyl}]hafnium dichloride, dimethylmethylene bis[1-{2-methyl-4-(4-biphenyl)-4H-azulenyl}]hafnium dichloride, dimethylgermylene bis[1-{2-methyl-4-(4-biphenylyl)-4H-azulenyl}]hafnium dichloride, dimethylsilylene bis{1-(2-ethyl-4-(3,5-dimethyl-4-trimethylsilylphenyl-4H-azulenyl)}hafnium dichloride, dimethylsilylene [1-{2-methyl-4-(4-biphenylyl)-4H-azulenyl}][1-{2-methyl-4-(4-biphenylyl)indenyl}]hafnium dichloride, dimethylsilylene {1-(2-ethyl-4-phenyl-4H-azulenyl)}{1-(2-methyl-4,5-benzindenyl)}hafnium dichloride, dimethylsilylene bis{1-(2-methyl-4-phenylindenyl)}hafnium dichloride, dimethylsilylene bis{1-(2-methyl-4,5-benzindenyl)

}hafnium dichloride, and dimethylsilylene bis[1-{2-methyl-4-(1-naphthyl)indenyl}]hafnium dichloride.

One of these transition metal-containing compounds (a) may be used alone, or two or more thereof may be used in combination. Among these transition metal-containing compounds (a), a chromium-containing compound is preferred, and among chromium-containing compounds, chromium (III) 2-ethylhexanoate is more preferred.

[Nitrogen-Containing Compound (b)]

In the present invention, the nitrogen-containing compound (b) (hereinafter, sometimes referred to as "catalyst component (b)") that is preferably used as a constituent component of the catalyst, is not particularly limited but includes amines, amides, imides, etc.

The amines include, for example, a pyrrole compound, and specific examples thereof include a pyrrole such as pyrrole, 2,4-dimethylpyrrole, 2,5-dimethylpyrrole, 2,5-diethylpyrrole, 2,4-diethylpyrrole, 2,5-di-n-propylpyrrole, 2,5-di-n-butylpyrrole, 2,5-di-n-pentylpyrrole, 2,5-di-n-hexylpyrrole, 2,5-dibenzylpyrrole, 2,5-diisopropylpyrrole, 2-methyl-5-ethylpyrrole, 2,5-dimethyl-3-ethylpyrrole, 3,4-dimethylpyrrole, 3,4-dichloropyrrole, 2,3,4,5-tetrachloropyrrole, 2-acetylpyrrole, indole, 2-methylindole and dipyrrole formed by combining two pyrrole rings through a substituent, and derivatives thereof.

The derivative includes, for example, a metal pyrrolide derivative, and specific examples thereof include aluminum pyrrolides such as diethylaluminum pyrrolide, ethylaluminum dipyrrolide, aluminum tripyrrolide, diethylaluminum (2,5-dimethylpyrrolide), ethylaluminum bis(2,5-dimethylpyrrolide), aluminum tris(2,5-dimethylpyrrolide), diethylaluminum (2,5-diethylpyrrolide), ethylaluminum bis(2,5-diethylpyrrolide) and aluminum tris(2,5-diethylpyrrolide, sodium pyrrolides such as sodium pyrrolide and sodium (2,5-dimethylpyrrolide), lithium pyrrolides such as lithium pyrrolide and lithium (2,5-dimethylpyrrolide), and potassium pyrrolides such as potassium pyrrolide and potassium (2,5-dimethylpyrrolide).

Here, the aluminum pyrrolides are not encompassed by the later-described aluminum-containing compound (c). In addition, the halogen-containing pyrrole compound is not encompassed by the later-described halogen-containing compound (d).

The amines may also be diphosphinoamines such as bis(diethylphosphino-ethyl)amine, bis(diphenylphosphino-ethyl)amine, N,N-bis(diphenylphosphino)methylamine and N,N-bis(diphenylphosphino)isopropylamine.

The amides include, for example, acetamide, N-methylhexanamide, succinamide, maleamide, N-methylbenzamide, imidazole-2-carboxamide, di-2-thenoylamine, β-lactam, δ-lactam, ε-caprolactam, and salts thereof with a metal of Groups 1, 2 or 13 of the periodic table.

The imides include, for example, 1,2-cyclohexanedicarboxyimide, succinimide, phthalimide, maleimide, 2,4,6-piperidinetrione, perhydroazecine-2,10-dione, and salts thereof with a metal of Group 1, 2 or 13 of the periodic table.

The sulfonamides and sulfonimides include, for example, benzenesulfonamide, N-methylmethanesulfonamide, N-methyltrifluoromethylsulfonamide, and salts thereof with a metal of Group 1, 2 or 13 of the periodic table.

One of these nitrogen-containing compounds (b) may be used alone, or two or more thereof may be used in combination.

In the present invention, among these, amines are preferred. Above all, a pyrrole compound is more preferred, and 2,5-dimethylpyrrole or diethylaluminum (2,5-dimethylpyrrolide) is still more preferred.

[Aluminum-Containing Compound (c)]

The aluminum-containing compound (c) (hereinafter, sometimes referred to as "catalyst component (c)") that is preferably used as a catalyst component of the present invention, is not particularly limited but includes, for example, a trialkylaluminum compound, an alkoxyalkylaluminum compound, a hydrogenated alkylaluminum compound, and an aluminoxane compound.

Here, a halogenated alkylaluminum compound is not encompassed by the aluminum-containing compound (c) and is encompassed by the later-described halogen-containing compound (d).

The trialkylaluminum compound includes, for example, trimethylaluminum, triethylaluminum, and triisobutylaluminum. The alkoxyaluminum compound includes, for example, diethylaluminum ethoxide.

The hydrogenated alkylaluminum compound includes, for example, a diethylaluminum hydride. The aluminoxane compound includes, for example, methylaluminoxane and ethylaluminoxane.

One of these aluminum-containing compounds (c) may be used alone, or two or more thereof may be used in combination. Among these, a trialkylaluminum compound is preferred, and triethylaluminum is more preferred.

[Halogen-Containing Compound (d)]

As the constituent component of the catalyst of the present invention, it is preferably to further contain (d) a halogen-containing compound (hereinafter, sometimes referred to as "catalyst component (d)"). The halogen-containing compound (d) is not particularly limited but includes, for example, an alkylaluminum halide compound, a benzylchloride skeleton-containing compound, a linear halogenated hydrocarbon containing two or more halogen atoms and having a carbon number of 1 or more, and a cyclic halogenated hydrocarbon containing one or more halogen atoms and having a carbon number of 3 or more.

The halogen-containing compound (d) includes, for example, an alkylaluminum halide-containing compound such as diethylaluminum monochloride, ethylaluminum sesquichloride and ethylaluminum dichloride, benzyl chloride, (1-chloroethyl)benzene, 2-methylbenzyl chloride, 3-methylbenzyl chloride, 4-methylbenzyl chloride, 4-ethylbenzyl chloride, 4-isopropylbenzyl chloride, 4-tert-butylbenzyl chloride, 4-vinylbenzyl chloride, α-ethyl-4-methylbenzyl chloride, α,α'-dichloro-o-xylene, α,α'-dichloro-m-xylene, α,α'-dichloro-p-xylene, 2,4-dimethylbenzyl chloride, 2,5-dimethylbenzyl chloride, 2,6-dimethylbenzyl chloride, 3,4-dimethylbenzyl chloride, 2,3,5,6-tetramethylbenzyl chloride, 1-(chloromethyl)naphthalene, 1-(chloromethyl)-2-methylnaphthalene, 1,4-bis-chloromethyl-2,3-dimethylnaphthalene, 1,8-bis-chloromethyl-2,3,4,5,6,7-hexamethylnaphthalene, 9-(chloromethyl)anthracene, 9,10-bis(chloromethyl)anthracene, 7-(chloromethyl)benzanthracene, 7-chloromethyl-12-methyl benzanthracene, methylene chloride, chloroform, carbon tetrachloride, 1,1-dichloroethane, 1,2-dichloroethane, 1,1,1-trichloroethane, 1,1,2-trichloroethane, 1,1,2,2-tetrachloroethane, pentachloroethane, hexachloroethane, 1,2,3-trichlorocyclopropane, 1,2,3,4,5,6-hexachlorocyclohexane, and 1,4-bis(trichloromethyl)-2,3,5,6-tetrachlorobenzene.

One of these halogen-containing compounds (d) may be used alone, or two or more thereof may be used in combination.

In the present invention, the ratio of respective constituent components, i.e., (a) a transition metal-containing compound, (b) a nitrogen-containing compound, (c) an aluminum-containing compound and (d) a halogen-containing compound which are catalyst components preferably used as the catalyst, is not particularly limited, but per mol of the transition metal-containing compound (a), the nitrogen-containing compound (b) is usually from 1 to 50 mol, preferably from 2 to 30 mol, and the aluminum-containing compound (c) is usually from 1 to 200 mol, preferably from 10 to 150 mol. In the case where the catalyst contains (d) a halogen-containing compound, the halogen-containing compound (d) is usually from 1 to 50 mol, preferably from 2 to 30 mol, per mol of the transition metal-containing compound (a).

In the present invention, the amount of the catalyst used is not particularly limited but is an amount to account for, in terms of the transition metal element of the transition metal-containing compound (a), usually from $1.0 \times 10^{-7}$ to 0.5 mol, preferably from $5.0 \times 10^{-7}$ to 0.2 mol, more preferably from $1.0 \times 10^{-6}$ to 0.05 mol, per liter of the later-described reaction solvent.

In the present invention, in the case of using ethylene as the α-olefin, the oligomerization reaction of ethylene is preferably performed by using a chromium-containing compound as the transition metal-containing compound (a) and contacting the ethylene with the chromium-containing compound as the transition metal-containing compound (a) in a mode of not previously contacting the transition metal-containing compound (a) with the aluminum-containing compound (c).

Thanks to such a contact mode, the trimerization reaction of ethylene can be selectively performed and 1-hexene as a trimer of ethylene can be obtained with a selectivity of 90% or more from the raw material ethylene. Furthermore, in this case, the ratio of 1-hexene in the hexene can be 99% or more.

The "mode of not previously contacting the transition metal-containing compound (a) with the aluminum-containing compound (c)" means that without being limited by the time of initiating the oligomerization reaction of ethylene, such a mode is maintained also in the subsequent additional feed of ethylene and catalyst components to the reactor. In addition, the same mode is preferably utilized also in the batch reaction form.

The contact mode in the above-described continuous reaction form includes the following (1) to (9):

(1) a method of simultaneously introducing the catalyst component (c) and a mixture of catalyst components (a), (b) and (d) into the reactor;

(2) a method of simultaneously feeding the catalyst component (a) and a mixture of catalyst components (b) to (d) to the reactor;

(3) a method of simultaneously feeding a mixture of catalyst components (a) and (b) and a mixture of catalyst components (c) and (d) to the reactor;

(4) a method of simultaneously feeding a mixture of catalyst components (a) and (d) and a mixture of catalyst components (b) and (c) to the reactor;

(5) a method of simultaneously feeding the catalyst component (c), the catalyst component (d) and a mixture of catalyst components (a) and (b) to the reactor;

(6) a method of simultaneously feeding the catalyst component (a), the catalyst component (b) and a mixture of catalyst components (c) and (d) to the reactor;

(7) a method of simultaneously feeding the catalyst component (b), the catalyst component (c) and a mixture of catalyst components (a) and (d) to the reactor;

(8) a method of simultaneously feeding the catalyst component (a), the catalyst component (d) and a mixture of catalyst components (b) and (c) to the reactor; and (9) a method of simultaneously and independently feeding respective catalyst components (a) to (d) to the reactor.

Each of the above-described catalyst components is usually dissolved in the below-described reaction solvent for use in the oligomerization reaction of ethylene and then fed to the reactor.

[Reaction Solvent]

In the production method of an α-olefin oligomer of the present invention, the oligomerization reaction of an α-olefin is performed in a reaction solvent.

The reaction solvent is not particularly limited, but a saturated hydrocarbon is preferably used. The saturated hydrocarbon is preferably a chain saturated hydrocarbon or an alicyclic saturated hydrocarbon, each having a carbon number of 3 to 20, such as butane, pentane, 3-methylpentane, n-hexane, n-heptane, 2-methylhexane, octane, cyclohexane, methylcyclohexane, 2,2,4-trimethylpentane and decalin.

In addition, an aromatic hydrocarbon such as benzene, toluene, xylene, ethylbenzene, mesitylene and tetralin, or the α-olefin oligomer itself produced by the oligomerization reaction, specifically, 1-hexene, decene, etc. obtained when trimerizing ethylene, may also be used. One of these solvents may be used alone, or a mixed solvent of two or more thereof may be used.

Among these solvents, from the standpoint that production or precipitation of a byproduct polymer such as polyethylene can be suppressed and furthermore, high catalytic activity tends to be obtained, a chain saturated hydrocarbon or alicyclic hydrocarbon having a carbon number of 4 to 10 is preferably used. Specifically, n-heptane or cyclohexane is preferred, and n-heptane is most preferred.

The amount of the reaction solvent used is not particularly limited but is, in terms of the mass ratio, usually from 0.5 to 5.0 times, preferably from 1.0 to 2.5 times, relative to the feed amount of the raw material α-olefin fed to the reactor.

EXAMPLES

The present invention is described more specifically below based on Examples. However, the present invention is not limited to the following Examples, as long as the gist thereof is observed.

Example 1

As shown in FIG. 1, in a process having a reactor 10 of a complete mixing and stirring type, a degassing tank 20, an ethylene separation column 30, a high boiling separation column 40 and a hexene separation column 50, a continuous oligomerization reaction [140° C., 71 kg/cm² (7.0 MPa)] of ethylene was performed.

From a first feed pipe 12, unreacted ethylene separated in the degassing tank 20 and the ethylene separation tank 30 was continuously fed to the liquid phase part of the reactor 10 by a compressor 60, together with ethylene newly fed from the ethylene feed pipe 12a.

From a second feed pipe 13, the recovered n-heptane separated in the hexane separation column 50 was continuously fed to the liquid phase part of the reactor 10. Furthermore, an n-heptane solution containing (a) chromium(III) 2-ethylhexanoate and (b) 2,5-dimethylpyrrole from a catalyst feed pipe 13a, and an n-heptane solution of (d) hexachloroethane from a catalyst feed pipe 13b through the second feed pipe 13, were continuously fed to the liquid phase part of the reactor 10. In addition, an n-heptane solution of (c) triethylaluminum was continuously fed from a third feed pipe 14 to the liquid phase part of the reactor 10.

Here, the catalyst was continuously fed to the liquid phase part of the reactor 10 such that the molar ratio of respective components fed to the reactor 10 becomes (a):(b):(c):(d)=1:25:80:5. After 2-ethylhexanol as a catalyst deactivator was added in an amount of 3 equivalents relative to the triethylaluminum (c) from a deactivator feed pipe 11a, the reaction product liquid continuously withdrawn from the reactor 10 was treated sequentially in the degassing tank 20, the ethylene separation column 30, the high boiling separation column 40 and the hexane separation column 50.

A mixed gas of the ethylene gas introduced into the reactor 10 and the vaporized vapor resulting from vaporization of part of the liquid phase due to the heat of polymerization produced by the oligomerization reaction of ethylene inside the reactor 10 was fed to a vertical multitubular heat exchanger 110 through piping 111 that is thermally insulated and kept warm. The mixed gas fed to the heat exchanger 110 was cooled by cooling water to afford an outlet temperature of 80° C., and the condensate liquid was again circulated and fed to the reactor 10 through piping 114.

Part of the vapor component obtained from the outlet of the heat exchanger 110 was separated into an ethylene gas and a condensate liquid in a gas-liquid separator 120 to which the gas component was fed through piping 112, and the ethylene gas was circulated and fed to the liquid phase part of the reactor 10 through piping 113, a blower 130 and piping 12. At this time, the actual gas linear velocity of the gas phase part of the reactor was about 1 cm/s.

The condensate liquid from the heat exchanger 110 was fed through piping 114 to the central part of an atomizer 10b of a rotating disc system provided in the gas phase part of the reactor 10, together with the condensate liquid from piping 115. The amount of liquid supplied to the atomizer was about 6% in terms of the volume ratio (about 30% in terms of the mass ratio) relative to the amount gas rising from the gas-liquid interface part of the reactor.

The atomizer 10b of a rotating disc system is provided 0.8 m above the gas-liquid interface L inside the reactor 10, where the ratio of the diameter of the rotating disc to the diameter of the reactor 10 is 0.5, and the condensate liquid is dispersed as droplets with a droplet diameter of approximately from 1 to 3 mm from the atomizer 10b of a rotating disc system.

At this time, the inlet temperature of the heat exchanger 110 (this temperature corresponds with the gas outlet temperature of the gas phase part of the reactor) was about 123° C. That is, the gas outlet temperature of the gas phase part of the reactor 10 is about 17° C. lower than the liquid phase temperature (140° C.).

After continuous operation for 100 days, the heat exchanger 110 was opened and inspected, as a result, it was confirmed with an eye that the surface of upper tube plate and the inner surface of tube (cooling transfer surface) of the heat exchanger 110 were not fouled.

Comparative Example 1

The process was performed thoroughly in the same manner except that in Example 1, the condensate liquid through piping 114 and piping 115 was not fed to the central part of the atomizer 10b but fed to the liquid phase part along the wall from the feed pipe to the gas phase part of the reactor 10 toward the inner wall inside the reactor 10. The inlet temperature of the heat exchanger 110 was about 133° C.

After continuous operation for 95 days, the heat exchanger 110 was opened and inspected, as a result, it was confirmed with an eye that polyethylene was thickly accumulated on the surface of upper tube plate of the heat exchanger 110 and plugged part of the tube.

While the invention has been described in detail and with reference to specific embodiments thereof, it will be apparent to one skilled in the art that various changes and modifications can be made therein without departing from the spirit and scope thereof. This application is based on a Japanese patent application filed on Sep. 22, 2014 (Application No. 2014-192685), the content thereof being incorporated herein by reference.

EXPLANATION OF REFERENCE SIGNS

10 Reactor
10a Stirrer
10b Atomizer
20 Degassing tank
30 Ethylene separation column
40 High boiling separation column
50 Hexene separation column
60 Compressor
100 Reflux condensation system
110 Heat exchanger
120 Gas-liquid separator
130 Blower

The invention claimed is:

1. A method for producing an α-olefin oligomer and reducing fouling in one or more downstream process equipment, comprising:
   oligomerizing an α-olefin in a reaction solvent in the presence of a catalyst in a reactor to produce the α-olefin oligomer comprising 1-hexene, wherein said reactor comprises a liquid phase and a gas phase;
   introducing a portion of the gas phase into a heat exchanger;
   cooling the portion of the gas phase in said heat exchanger to obtain a condensate liquid; and
   dispersing the condensate liquid as droplets in the gas phase inside said reactor by an atomizer of a rotating disk spray system;
   wherein said gas phase comprises a mist comprising a component of the catalyst and/or a portion of the α-olefin, wherein the mist is generated by vaporization of the liquid phase, and wherein the mist is absorbed onto the condensate droplets thereby reducing fouling in the downstream process equipment caused by the mist.

2. The method of claim 1, wherein said heat exchanger is arranged outside of said reactor.

3. The method of claim 1, wherein the gas outlet temperature of the gas phase of said reactor is lower by 8° C. or more than the liquid phase temperature of said reactor.

4. The method of claim 1, wherein the inlet temperature of said heat exchanger is lower by 8° C. or more than the liquid phase temperature of said reactor.

5. The method of claim 1, wherein an uncondensed gas obtained from said heat exchanger is fed to the liquid phase of said reactor.

6. The method of claim 1, wherein said catalyst comprises a combination of a chromium-containing compound, a nitrogen-containing compound (b), and an aluminum-containing compound (c).

7. The method of claim 6, wherein said catalyst further comprises a halogen-containing compound (d).

8. The method of claim 1, wherein said α-olefin is ethylene.

9. The method of claim 1, wherein a ratio of the diameter of the rotating disk of the atomizer to the diameter of the reactor is in a range from 0.1 to 0.8.

10. The method of claim 1, wherein the condensate droplets have a diameter of 0.05 to 5 mm.

* * * * *